United States Patent
Sonke et al.

(10) Patent No.: US 7,241,602 B2
(45) Date of Patent: Jul. 10, 2007

(54) NUCLEIC ACID SEQUENCES ENCODING ENANTIOSELECTIVE AMIDASES

(75) Inventors: Theodorus Sonke, Guttecoven (NL); Renate Francisca Tandler, Buchten (NL); Cornelis Gerrit Nijs Korevaar, Katwijk (NL); Friso Bernard Jan Van Assema, Geleen (NL); Rudolf Van Der Pol, Schiedam (NL)

(73) Assignee: DSM IP Assets B.V., TE Heerlen (NL)

( * ) Notice: Subject to any disclaimer, the term of this patent is extended or adjusted under 35 U.S.C. 154(b) by 135 days.

(21) Appl. No.: 10/484,681

(22) PCT Filed: Jul. 15, 2002

(86) PCT No.: PCT/NL02/00471

§ 371 (c)(1),
(2), (4) Date: Sep. 30, 2004

(87) PCT Pub. No.: WO03/010312

PCT Pub. Date: Feb. 6, 2003

(65) Prior Publication Data
US 2005/0079595 A1    Apr. 14, 2005

(30) Foreign Application Priority Data

Jul. 23, 2001  (EP) .................... 01202821
Jul. 23, 2001  (EP) .................... 01202822

(51) Int. Cl.
| | |
|---|---|
| C12N 9/86 | (2006.01) |
| C12N 9/04 | (2006.01) |
| C12N 9/10 | (2006.01) |
| C12N 1/20 | (2006.01) |
| C12P 21/06 | (2006.01) |
| C12P 13/04 | (2006.01) |
| C07H 21/04 | (2006.01) |

(52) U.S. Cl. ............... 435/129; 435/69.1; 435/91.1; 435/106; 435/191; 435/193; 435/231; 435/227; 435/252.3; 435/320.1; 435/136; 536/23.2

(58) Field of Classification Search ............. 435/220, 435/69.7, 252.8
See application file for complete search history.

(56) References Cited

U.S. PATENT DOCUMENTS 4,080,259 A   3/1978  Boesten et al.
5,248,608 A   9/1993  Van Dooren et al.
6,617,139 B1 * 9/2003  Nakamura et al. .......... 435/106

FOREIGN PATENT DOCUMENTS

| EP | 0 494 716 | 7/1992 |
| EP | 1 174 499 | 1/2002 |
| WO | WO 99/61633 | 12/1999 |
| WO | WO-00/63354 | 10/2000 |
| WO | WO-00/66751 | 11/2000 |

OTHER PUBLICATIONS

International Search Report for PCT/NL02/00471, mailed on Jun. 27, 2003, 3 pages.
Kaptein et al., Tetrahedron (2001) 57:6567-6577.
Komeda et al., European Journal of Biochemistry (2000) 267:2028-2035.
Makrides, Microbiological Reviews (1996) 60:512-538.
Mayaux et al., Journal of Bacteriology (1990) 172:6764-6773.
Tweel et al., Applied Microbiology and Biotechnology (1993) 39:296-300.
Sonke et al. "Purification and characterization of an L-specific amidase from *Ochrobactrum anthropi* NCIMB 40321" in *Beijerinck Centennial—Microbial Physiology and Gene Regulation: Emerging Principles and Applications*, Scheffers & van Dijken, eds. (Delft, NL: Delft University Press) pp. 456-457 (1995).

* cited by examiner

Primary Examiner—Rebecca E. Prouty
Assistant Examiner—Ganapathirama Raghu
(74) Attorney, Agent, or Firm—Nixon & Vanderhye P.C.

(57) ABSTRACT

The invention relates to nucleic acid sequence encoding enantioselective amides with an amino acid sequence of SEQ ID NO: 2. The invention also relates to a process for fermentation, comprising a batch and a feed phase, of a microorganism in a fermentation medium, wherein the microorganism expresses a nucleic acid according to the invention and wherein between 0.5 and 50 mg of $Zn^{2+}$/ml of fermentation medium is fed during the fermentation. The invention also relates to a process for the preparation of enatiomerically enriched carboxylic acid and/or an enatiomerically enriched carboxylic acid amide, in which a mixture of corresponding D- and L-carboxylic acid amides is contacted with a expression product according to the invention in the presence of 0.01 mM–100 mM $Zn^{2+}$, whereby one of the enantiomers of the carboxylic acid amide is enatiomerically hydrolysed to from corresponding enatiomerically enriched carboxylic acid, while the other enantiomer of the carboxylic acid amide remains unchanged.

12 Claims, 1 Drawing Sheet

NUCLEIC ACID SEQUENCES ENCODING ENANTIOSELECTIVE AMIDASES

CROSS-REFERENCE TO RELATED APPLICATION

This application is the national phase of PCT application PCT/NL02/00471 having an international filing date of 15 Jul. 2002, which claims priority from European applications 01202822.1 and 01202821.3, both filed 23 Jul. 2001. The contents of these documents are incorporated herein by reference.

The invention relates to nucleic acid sequences encoding enantioselective amidases. The invention also relates to vectors, and host cells comprising the nucleic acid sequences according to the invention as well as processes for producing and using the expression products of the nucleic acid sequences.

Amidases are polypeptides with amidase activity and are enzymes with the ability to catalyze the hydrolysis of carboxylic acid amides to form the corresponding carboxylic acids and ammonia. Enantioselective amidases are amidases with a preference for one of the enantiomers of a carboxylic acid amide as a substrate. Enantioselective amidases are known to be valuable in commercial bioprocesses in the production of enantiomerically enriched carboxylic acids. Carboxylic acids are for example α-H-α-amino acids, α,α-dialkylamino acids, α-hydroxy acids and/or derivatives thereof as well as peptides thereof. Enantiomerically enriched carboxylic acids-and/or derivatives thereof as well as peptides are used in various industries, as for example the pharmaceutical industry, the agrochemical industry etc. For example, the amino acid L-valine is highly suitable as a precursor in cyclosporin A fermentations, α-hydroxypropionic acid is used in the production of herbicides, some α-N-hydroxyamino acids can be used as anti-tumor agents and D-p-hydroxyphenylglycine and D-phenylglycine are used in the production of certain semisynthetic broad-spectrum β-lactam antibiotics. In EP 494 716 B1, two examples of microorganisms displaying amidase activity are given: *Ochrobactrum anthropi* NCIB 40321 (also known as NCIMB 40321) and *Klebsiella* sp. NCIB 40322.

The invention specifically relates to nucleic acid sequences encoding enantioselective amidases with an amino acid sequence, which has at least 70% identity with SEQ ID: NO. 2. In SEQ ID: NO. 1 the nucleic acid sequence encoding the L-amidase from *Ochrobactrum anthropi* NCIMB 40321 is presented. In SEQ ID: NO. 2, the amino acid sequence corresponding to the nucleic acid sequence of SEQ ID: NO. 1 is presented. It has surprisingly been found that a fermentation, comprising a batch phase and a feed phase, of a microorganism expressing a nucleic acid encoding an enantioselective amidase with an amino acid sequence, which has at least 70% identity with SEQ ID: NO. 2 in a fermentation medium results in an increased production of enantioselective amidase activity if in the feed phase between 0.5 and 50 mg/l fermentation medium $Zn^{2+}$ is fed to the fermentation medium.

This increased production of enantioselective amidase activity is probably due to an increase in activity of the enantioselective amidase itself as well as to an increase in the amount of enantioselective amidase produced. In EP 1,174,499 A1 a nucleic acid sequence encoding an enantioselective amidase from *Enterobacter cloacae* N-7901 has been disclosed; the corresponding amino acid sequence has 68% identity with the amino acid sequence corresponding to the nucleic acid sequence of SEQ ID NO: 1. The nucleic acid sequences encoding enantioselective amidases according to the invention are therefore new. The $Zn^{2+}$ dependency of the fermentation of the microorganism expressing the nucleic acid sequence encoding an enantioselective amidase of *Enterobacter cloacae* N-7901 has not been described in EP 1,174,499.

The present invention preferably relates to nucleic acid sequences encoding enantioselective amidases with amino acid sequences, which have a degree of identity with SEQ ID NO. 2 of at least about 75%, more preferably at least about 80%, even more preferably at least about 85%, most preferably at least about 90%, more preferably at least 95% and even more preferably at least 97%, in particular at least 98%, more in particular at least 99%, most in particular 100%.

For purpose of the present invention, the degree of identity between two amino acid sequences is determined by the BLASTP pairwise alignment algorithm (NCBI) with an identity table and the following alignment parameters: Mismatch=−15, Penalty=−3, Gap-Extend=1, Match-Bonus=1, Gap x-droff=50, Expect=10, Word Size=3.

The present invention also relates to nucleic acid sequences encoding enantioselective amidases, which nucleic acid sequences preferably hybridize under medium, more preferably under high stringency conditions and most preferably very high stringency conditions with (i) SEQ ID NO. 1, (ii) a genomic DNA sequence comprising SEQ ID NO.1 or (iii) a complementary strand of (i) or (ii).

Hybridization experiments can be performed by a variety of methods, which are well available to the skilled man. General guidelines for choosing among these various methods can be found in e.g. chapter 9 of Sambrook, J., Fritsh, E. F., and Maniatis, T. Molecular Cloning: A Laboratory Manual. 2nd ed., Cold Spring Harbor Laboratory, Cold Spring Harbor Laboratory Press, Cold Spring Harbor, N.Y., 1989.

With stringency of the hybridization conditions is meant, the conditions under which the hybridization, consisting of the actual hybridization and wash steps, are performed. Wash steps are used to wash off the nucleic acids, which do not hybridize with the target nucleic acid immobilized on for example a nitrocellulose filter. The stringency of the hybridization conditions can for example be changed by changing the salt concentration of the wash solution and/or by changing the temperature under which the wash step is performed (wash temperature). Stringency of the hybridization increases by lowering the salt concentration in the wash solution or by raising the wash temperature. For purpose of this application, the hybridization is performed in 6× sodium chloride/sodium citrate (SSC) at about 45° C. for about 12 hours. Two consecutive 30 minutes wash steps in 1×SSC, 0.1% SDS at 50° C. is an example of low stringency, at 55° C. an example of medium stringency, at 60° C. an example of high stringency, at 65° C. an example of very high stringency.

The invention also relates to nucleic acid sequences encoding enantioselective amidases with an amino acid sequence according to SEQ ID: NO. 2 with alterations at about 15 or less amino acid positions, preferably at about 10 or less amino acid positions, more preferably at about 5 or less, even more preferably at about 3 or less amino acid positions, wherein the alteration(s) are/is independently (i) an insertion of an amino acid (ii) a deletion of an amino acid (iii) a substitution of an amino acid.

Nucleic acid sequences encoding enantioselective amidases with an amino acid sequence given in SEQ ID: NO. 2 with a number of alterations, can be prepared in a manner known in the art, for instance with site-directed mutagenesis of the nucleic acid sequence. In this method a mutagenic oligonucleotide encoding the desired mutation(s), such as a substitution, insertion or deletion on a specific amino acid position, is annealed to one strand of the DNA of interest and serves as a primer for initiation of DNA synthesis. By DNA synthesis a mutagenic oligonucleotide is incorporated into the newly synthesized strand. Often, the methods known in the art also have a positive selection technique for mutagenic nucleic acid sequences in order to enhance the efficiency of the site-directed mutagenesis method. Some site-directed mutagenesis techniques make use of PCR, in which a mutagenic oligonucleotide is used as a primer. Methods for achieving site-directed mutations are described in various product folders of companies, as for example Stratagene and Invitrogen and kits for achieving site-directed mutations are commercially available.

The present invention also relates to nucleic acid sequences encoding enantioselective amidases, which display immunological cross-reactivity with an antibody raised against a fragment of the amino acid sequence according to SEQ ID: NO. 2. The length of each fragment is preferably at least 20 amino acids. The immunological cross reactivity may be assayed using an antibody raised against, or reactive with, at least one epitope of the isolated polypeptide according to the present invention having amidase activity. The antibody, which may either be monoclonal or polyclonal, may be produced by methods known in the art, e. g. as described by Hudson et al., Practical Immunology, Third Edition (1989), Blackwell Scientific Publications. The immunochemical cross-reactivity may be determined using assays known in the art, an example of which is Western blotting, e. g. as described in Hudson et al., Practical Immunology, Third Edition (1989), Blackwell Scientific Publications.

The present invention also relates to nucleic acid sequences encoding enantioselective amidase fusion proteins, which consist of a nucleic acid encoding a polypeptide according to the invention operatively linked to one or more nucleic acid sequences, which encode (a) marker polypeptide(s). With operatively linked is meant, that the two nucleic acid sequences are linked such that, if expressed, the enantioselective amidase fusion protein is produced with the marker polypeptide on its N- and/or C-terminus. The marker polypeptide can serve many purposes, for example, it may be used to increase the stability or the solubility of the fusion protein, it may be used as a secretion signal, which is a signal that directs the fusion protein to a certain compartment in the cell or it may be used to facilitate purification of the fusion protein. Examples of marker polypeptides used to facilitate purification of the fusion protein are the MBP- and the GST-tag. The purification of a fusion protein with a MBP-tag or a GST-tag is for example described in F. M. Ausubel, R. Brent, R. E. Kingston, D. D. Moore, J. G. Seidman, J. A. Smith, and K. Struhl eds., Current Protocols in Molecular Biology, John Wiley & Sons, Inc., New York, N.Y., USA, 1990. A fusion protein with anMBP-tag can for example be produced in a pMAL vector (New England Biolabs, Beverly, Mass., USA), whereas a fusion protein with a GST-tag can be produced in a pGEX vector (Amersham Biosciences, Inc., Piscataway, N.J., USA) by following the protocol of the respective supplier.

A nucleic acid sequence of the present invention, for example the nucleic acid sequence with the sequence of SEQ ID: NO. 1 can be isolated using standard molecular biology techniques and the sequence information provided herein. For example, using all or a portion of the nucleic acid sequence of SEQ ID: NO. 1 on Ochrobactrum anthropi NCIB 40321 as a hybridization probe, a nucleic acid sequence according to the invention can be isolated using standard hybridization and cloning techniques (e. g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989).

Moreover, a nucleic acid sequence encompassing all or a portion of SEQ ID: NO. 1 can be isolated by the polymerase chain reaction (PCR) using synthetic oligonucleotide primers designed based upon the sequence information contained in SEQ ID: NO. 1 or SEQ ID: NO. 2, by using PCR on Ochrobactrum anthropi NCIB 40321 and might also be isolated if the oligonucleotide primers are used on a microorganism displaying enantioselective amidase activity.

A nucleic acid sequence of the invention may also be amplified using for example genomic DNA, cDNA or alternatively the appropriate mRNA from a microorganism displaying enantioselective amidase activity, as a template and appropriate oligonucleotide primers based upon the sequence information provided herein according to standard (RT)-PCR amplification techniques. The nucleic acid so amplified can be cloned into a suitable vector and characterized by DNA sequence analysis.

Furthermore, oligonucleotides corresponding to or hybridizable to nucleic acid sequences according to the invention can be prepared by standard synthetic techniques, e.g., using an automated DNA synthesizer.

The nucleic acid sequences according to the invention can be cloned in a suitable vector and after introduction in a suitable host, the sequence can be expressed to produce the corresponding enantioselective amidases according to standard cloning and expression techniques, which are known to the person skilled in the art (e. g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989). The invention also relates to such vectors comprising a nucleic acid sequence according to the invention.

Suitable vectors are the vectors normally used for cloning and expression and are known to the person skilled in the art. Examples of suitable vectors for expression in E. coli are given e.g. in table 1 in Makrides, S. C., Microbiological Reviews, Vol. 60, No. 3, (1996), 512–538. Preferably, the vector contains a promoter upstream of the cloning site containing the nucleic acid sequence encoding the polypeptide with amidase activity, which can be switched on after the host has been grown to express the corresponding polypeptide having amidase activity. Promoters, which can be switched on and off are known to the person skilled in the art and are for example the lac promoter, the araBAD promoter, the T7 promoter, the trc promoter, the tac promoter and the trp promoter. Particularly useful in the framework of the invention are for example the vectors as described in WO 00/66751, e.g. pKAFssECtrp or pKAFssECaro without the insert, the penicillin G acylase gene. Suitable hosts are the hosts normally used for cloning and expression and are known to the person skilled in the art.

Examples of suitable host strains are for example *Echerichia coli* strains, e.g. *E. coli* TOP10F', TOP10, DH10B, DH5α, HB101, W3110, BL21(DE3) and BL21 (DE3)pLysS. Particularly useful in the framework of the invention are *Escherichia coli* K-12 strains, e.g. DH1, HB101, RV308, RR1, W3110, C600.

The choice of the vector can sometimes depend on the choice of the host and vice versa. If e.g. a vector with the araBAD promoter is being used, an *E. coli* host strain that is unable to break down the arabinose inducer (ara-), is strongly preferred.

Alternatively, the nucleic acid sequences according to the invention can be integrated into the genome of a host cell, which does not normally contain a nucleic acid sequence according to the invention and be (over)expressed. This can be done according to methods known to the person skilled in the art. The invention also relates to a host cell, which does not normally contain a nucleic acid sequence according to the invention, comprising a nucleic acid sequence according to the invention, preferably to a host cell comprising a vector comprising a nucleic acid sequence according to the invention.

The invention also relates to a process for the preparation of the expression product of a nucleic acid sequence according to any of claims 1–5 wherein in a first step the nucleic acid sequence is introduced into a suitable host, which does not normally contain a nucleic acid sequence according to the invention, and wherein the nucleic acid sequence is subsequently expressed in said host. The introduction of a nucleic acid sequence and the subsequent expression are standard techniques known to the person skilled in the art.

The invention also relates to a process for the fermentation, comprising a batch and a feed phase, of a microorganism in a fermentation medium, wherein the microorganism expresses a nucleic acid according to the invention and wherein between 0.5 and 50 mg/l_fermentation medium (corresponding to between 7.7 µM and 770 µM) $Zn^{2+}$ is fed during the fermentation.

Typically, the feed phase is started after approximately 10 hours. The amount of $Zn^{2+}$ of 0.5–50 mg/l_fermentation medium can be fed at once to the fermentation medium, but is preferably dosed, as the addition of $Zn^{2+}$ at once gives rise to the formation of foam on the fermentation medium and to lysis of the microorganism later on in the fermentation. $Zn^{2+}$ can be dosed in for example 5–10 equal portions, but of course it is also possible to dose $Zn^{2+}$ in different portions during the feed phase. Preferably, $Zn^{2+}$ is continuously fed to the fermentation medium. If a continuous feed is used, it is very practical to combine $Zn^{2+}$ with other components in one feed.

$Zn^{2+}$ ions are for example present in zincsalts. In the process according to the invention preferably zinc salts that are well solvable in water (more than 0.1 moles per liter) are used, for example $Zn(NO_3)_2$, $Zn(CH_3COO)_2$, $ZnSO_4$, $ZnCl_2$, $ZnBr_2$, $ZnI_2$.

The microorganism used in the fermentation can be a microorganism, which possesses and expresses a nucleic acid sequence according to the invention by nature, but is preferably a host in which the nucleic acid sequence according to the invention is expressed, more preferably overexpressed.

It has been found that the enantioselective amidase activity of an expression product of a nucleic acid sequence according to the invention is also improved in the presence of between 0.01 mM and 100 mM $Zn^{2+}$. Therefore, the invention also relates to a process for the preparation of an enantiomerically enriched carboxylic acid and/or an enantiomerically enriched carboxylic acid amide, in which a mixture of the corresponding D- and L-carboxylic acid amides is contacted with an expression product according to any of claims 1–5 in the presence of between 0.01 mM and 100 mM $Zn^{2+}$, whereby one of the enantiomers of the carboxylic acid amide is enantioselectively hydrolysed to form the corresponding enantiomerically enriched carboxylic acid, while the other enantiomer of the carboxylic acid amide remains unchanged. If desired, the remaining enantiomerically enriched carboxylic acid amide can be hydrolysed to form the corresponding enantiomerically enriched acid. The hydrolysis of the remaining carboxylic acid amide can be performed with methods known in the art, for instance under basic or acidic conditions, or enzymatically.

Preferably, the enantioselective hydrolysis catalyzed by the expression product of a nucleic acid sequence according to the invention is performed in the presence of between 0.01 and 50, more preferably between 0.05 and 20 mM $Zn^{2+}$.

The pH at which the enantioselective hydrolysis catalyzed by the expression product of a nucleic acid sequence according to the invention, takes place is not critical, preferably the enantioselective hydrolysis is performed at a pH between 5 and 9, more preferably between 6.5 and 8.5.

The temperature at which the enantioselective hydrolysis in the presence of an expression product according to the invention takes place is preferably between 10 and 75° C., more preferably between 30 and 65° C., in particular between 40 and 60° C.

As a mixture, racemic mixtures of D- and L-carboxylic acid amide can be used, but of course it is also possible to use randomly chosen mixtures of D- and L-carboxylic acid amide.

Examples of suitable carboxylic acid amides are: α-H-α-amino acid amides with 2–20 C-atoms or derivatives thereof, as for example alanine amide, phenylglycine amide, phenylalanine amide, para-hydroxyphenylglycine amide, proline amide, valine amide, leucine amide, tertiary leucine amide, methionine amide, proline amide, glutamic acid amide, α-H-α-hydroxy acid amides with 2–20 C-atoms, for example mandelic acid amide, α-α-dialkyl-amino acid amides with 2–20 C-atoms, for example α-methylvaline amide, α-methylphenylglycine amide, α-ethylphenylglycine amide, α-butylphenylglycine amide, α-methylphenylalanine amide, α-ethylphenylalanine amide, α-ethyl-α-butyl glycine amide. Preferably tert-leucine or α-methylphenylglycine is prepared in a process according to the invention.

By way of illustration of the invention, the following examples have been added.

EXAMPLES

Example 1

Fermentation of *Escherichia coli* K-12 Expressing the Nucleic Acid Sequence Presented in SEQ ID: NO. 1 with the Addition of $Zn^{2+}$ to the Fermentation Medium in the Feed Phase The following seed medium was prepared:

| | |
|---|---|
| Yeast extract powder (DIFCO, Bacto ™) | 38 g |
| Na₂HPO₄ | 17.8 g |
| KH₂PO₄ | 13.6 g |
| NH₄Cl | 4.8 g |
| Distilled water | 1500 ml |

The pH was adjusted to 6.8 with aqueous NaOH. 100 and 200 ml aliquots were placed in 500 and 2000 ml Erlenmeyer flasks and sterilised (20 min. at 121° C.). 1.1 ml of a 50% (w/v) glucose and 2.2 ml of a neomycin (1.2 g/l) solution were aseptically added to the 500 ml flask (seedphase 1). 1 and 2 ml of the 50% (w/v) glucose and neomycin (1.2 g/l) solution were added to the 2000 ml flask (seedphase 2).

The Erlenmeyer flask of seedphase 1 was then seeded with a 1.8 ml 50% v/v glycerol/water suspension of the *E. coli* K-12 strain expressing the nucleic acid sequence according to SEQ ID: NO 1 and the whole was cultured and incubated for 22 hours at 27° C. under constant orbital agitation. To express the nucleic acid sequence presented in SEQ ID NO. 1, in the *E. coli* K-12 strain RV308, the nucleic acid sequence was amplified by PCR using amidase specific primers with 5'-extensions containing a restriction site (NdeI for forward and SmaI for reverse primer). The obtained fragment was cloned into a derivative of *E. coli* expression vector pKECtrp at the site of *E. coli* penicillin G acylase encoding sequence using restriction enzymes NdeI and SmaI. The derivative expression vector used is similar to construct pKECtrp, whose construction has been described in WO 00/66751, except that it contains the *E. coli* aro promoter instead of the trp promoter. The whole seedphase 1 Erlenmeyer flask was used to inoculate the 2000 ml Erlenmeyer flask of the seedphase 2. Seedphase 2 was cultured and incubated for 3 hours at 27° C. under constant orbital agitation.

2% (v/v) of seedphase 2 was used to inoculate 6.4 l of batch phase medium in a 20 l glass fermentor. The batch phase medium had the following composition:

| | |
|---|---|
| Gistex ® LS pasta | 24.6 g/l |
| Citric acid | 10 g/l |
| FeSO₄.7H₂O | 0.2 g/l |
| MgSO₄.7H₂O | 3.1 g/l |
| CaCl₂.2H₂O | 1.5 g/l |
| MnSO₄.H₂O | 0.169 g/l |
| (NH₄)₂SO₄ | 9.0 g/l |
| CoCl₂.6H₂O | 0.006 g/l |
| NaMoO₄.2H₂O | 0.004 g/l |
| H₃BO₃ | 0.004 g/l |
| Antifoam: Basildon 86/013 | few drops |
| K₂HPO₄[1] | 8.1 g/l |
| Dextrose[2] | 11.4 g/l |
| Neomycine[2] | 0.012 g/l |
| Thiamine[2] | 0.014 g/l |

The batch phase medium was sterilised at 121° C. for 65 minutes, after adjusting the pH to 4.5 (with NaOH). The medium components marked with [1] and [2] were each dissolved separately and the solution comprising the components marked with [1] were sterilised at 121° C. for 65 minutes and solutions comprising the components marked with [2] were filter-sterilised. Both were added aseptically to the medium. Before the transfer of the seedphase 1, the pH of the batch phase medium was adjusted to pH 7.0. The fermentation was conducted at 27° C. under constant stirring and optimal aeration conditions. Between 50 and 54 hours, the temperature of the fermentation was linearly decreased during 4 hours from 27 to 25° C. and maintained at that value till the end of the fermentation.

During the fermentation (batch and feed phase), the pH was allowed to variate between 7.00 and 7.30. The batch phase was ended with the start of feed 1 and feed 2 (beginning of the feed phase) when the pH reached the level of 7.15. At that moment, the carbon source was exhausted. The batch phase had a duration of approximatively 9 hours. Feed 1 had the following composition:

| | |
|---|---|
| Dextrose | 670 g/l |
| Thiamine[1] | 0.18 g/l |
| MgSO₄.7H₂O[1] | 14.4 g/l |
| Proline[1] | 6.1 g/l |
| Monosodiumglutamate[1] | 12.2 g/l |
| ZnSO₄.7H₂O[1] | 0.022 g/l |

Feed 1 was prepared as follows. The dextrose was first dissolved. About 0.4 ml/l 4N HCl was added to the dextrose solution. The solution was sterilised (121° C. for 30 minutes). Thiamine, MgSO₄.7H₂O, proline and monosodiumglutamate and ZnSO₄.7H₂O were dissolved separately and the solution was filter-sterilised before addition (aseptically) to the dextrose solution. The profile used to introduce feed 1 into the batch phase medium is given below in table 1.

TABLE 1

Feed profile used to introduce feed 1.

| Time | Setpoint [$g_{feed}/(l_{start}*h)$] |
|---|---|
| 0 (Feedstart)–14 hours | $2.59 \times e^{(0.07 \times Time)}$ |
| 14–40 hours | $6.91 + 0.48 \times (Time - 14)$ |
| 40 hours–end of fermentation | 19.3 |

Feed 2 had the following composition:

Gistex® LS pasta 300 g/l

Feed 2 was prepared as follows. The yeast extract paste was first dissolved in water. Subsequently, the pH was adjusted to 4.5+/−0.1. The solution was sterilised (121° C. for 30 minutes). The profile used to introduce feed 2 into the batch phase medium is given below in table 2. With 'Time' in the profiles of table 1 and 2 is meant 'hours after feedstart'.

TABLE 2 profile used to introduce feed 2.

| Time | Setpoint [$g_{feed}/(l_{start}*h)$] |
| --- | --- |
| 0 (Feedstart)–14 hours | $0.81 \times e^{(0.07 \times Time)}$ |
| 14–34 hours | $2.15 + 0.15 \times (Time - 14)$ |
| 34–38 hours | 5.15 |
| 38 hours–end of fermentation | 0 |

Feed 1 and feed 2 constitute the feed phase medium. The fermentation was terminated after 120 hours.

The fermentation was repeated with the exception that in feed 1 no $ZnSO_4.7H_2O$ was present.

The L-amidase activity in the fermentation broth (fermentation medium and cells) after start of the feed phase was determined for both fermentations in the manner as described below:

Analysis of the L-amidase Activity of Fermentation Broth (Fermentation Medium with Cells) Samples Obtained from the Fermentation of *Escherichia coli* K-12 Expressing the Nucleic Acid Sequence Presented in SEQ ID: NO. 1 with $Zn^{2+}$ in Feed 1 and without $Zn^{2+}$ in Feed 1

1.5 ml of incubation reagent (containing 1.1 w % L-phenylglycine amide, 0.11 M HEPES-NaOH buffer, pH 8.0 and 1.1 mM $MnSO_4.1H_2O$) was heated in a waterbath to 55° C. After 10 minutes, 100 µl of a sample solution (containing fermentation broth diluted in 20 mM HEPES-NaOH, pH 7.5/2 mM DTT) was added to the heated incubation reagent. After incubation of the combined incubation reagent with sample solution for 20 minutes, the reaction was stopped by adding 100 µl of the combined incubation reagent to 1.5 ml stop reagent (53 mM phosphoric acid). The stopped reaction mixture was centrifuged for 5 minutes at 14,000 rpm. The supernatant was analysed with HPLC under the following conditions:
column: nucleosil 120-3C18 (125×4 mm)
wavelength detector: 220 nm
flow: 1.0 ml/min
injection volume: 20 µl
eluent: 100 mM phosphate buffer pH 3.0
Retention times of L-phenylglycine and L-phenylglycine amide are respectively about 1.8 and 2.7 minutes.

The area under the HPLC peak corresponding to phenylglycine was calculated and after correction for the dilution factor of the fermentation broth, compared to the area under the phenylglycine peak from other samples. The relative peak areas from the samples are equal to the relative L-amidase activity, which is the activity of the samples as compared to one another. The relative L-amidase activity (rel. act.) of the samples from the fermentation with a feed 1 with $Zn^{2+}$ (A) and with a feed 1 without $Zn^{2+}$ (B) is presented in FIG. 1, in which the relative activity has been plotted against T (h), the time (in hours after start of the batch phase) at which the samples were taken.

Figure 1:
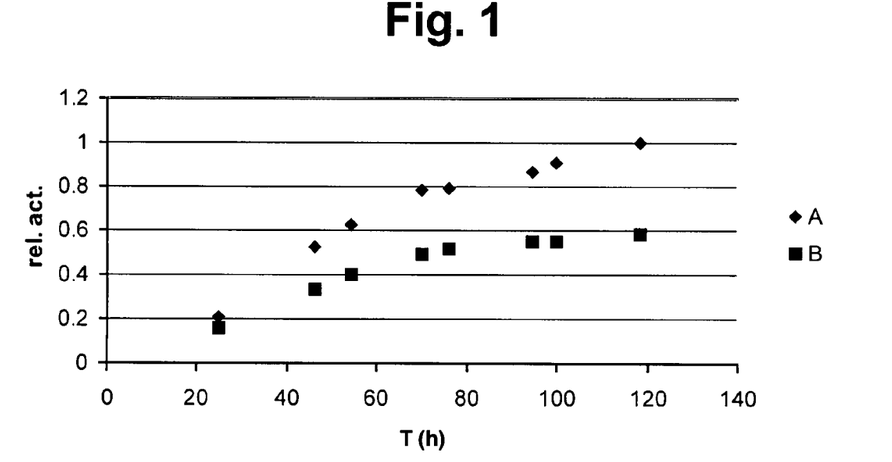
FIG. 1: The relative L-amidase activity (rel.act.) of the samples from fermentation with a feed 1 with $Zn^{2+}$ (A) and with a feed 1 without $Zn^{2+}$ (B).

From FIG. 1, it can be seen that if $Zn^{2+}$ is fed to the fermentation in the feed phase, more L-amidase activity is produced.

Preparation of the Enzyme Solution LAM0011 from the Fermentation with $Zn^{2+}$ in Feed 1

The fermentation broth from the fermentation with $Zn^{2+}$ in feed 1 was treated with 4 g/l octanol in the fermentation to kill the microorganisms and was homogenized twice by high pressure homogenization (600–700 bars). After homogenization the broth was flocculated by addition of 10 v %, calculated on the volume of broth of a 10% solution of C577. 10 v %, calculated on broth volume, of Dicalite 448, a filter aid, was added. The resulting slurry was filtered over a membrane filterpress and washed with 1 cake volume of process water. The biomass cake was sent to incineration. The filtrate was filtrated over Seitz filterplates (sizes 5–15 µm) followed by 0.1–0.3 micrometer germ filtration plates. The resulting filtrate was stored in containers and frozen until use.

Preparation of the Enzyme Solution LAM0001 from the Fermentation without $Zn^{2+}$ in Feed 1.

The fermentation broth from the fermentation without $Zn^{2+}$ in feed 1 was treated with 4 g/l octanol in the fermentation to kill the microorganisms and was homogenized twice by high pressure homogenisation (600–700 bars). After homogenisation the broth was flocculated by addition of 10% on the volume of broth of a 10% solution of C577. 10 v %, calculated on broth volume, of Dicalite 448, a filter aid, was added. The resulting slurry was filtered over a membrane filterpress and washed with 2,2 cake volumes of process water. The biomass cake was sent to incineration. The filtrate was filtrated over Seitz filterplates sizes 5–15 micrometer followed by 0.1–0.3 micrometer germ filtration plates. Hereafter the resulting filtrate was concentrated a factor 3 using 50 kD Polysulphon membranes. The retentate was washed with a quarter of the retentate volume of RO water. The retentate was hereafter again filtrated over Seitz filterplates sizes 5–15 micrometer followed by 0.1–0.3 micrometer germ filtration plates. The resulting filtrate was stored into containers and frozen until use in the application reaction (examples 2–5).

Example 2

Enantioselective Hydrolysis of
DL-α-methylphenylglycine Amide in the Presence
of Different Concentrations of $Zn^{2+}$ at pH 6.5
Using L-amidase from *Ochrobactrum anthropi*
NCIMB 40321

The effect of the $Zn^{2+}$ concentration on the hydrolysis reaction of DL-α-methylphenylglycine amide with the L-amidase from *O. anthropi* NCIMB 40321, was determined by performing this reaction in the presence of 0.1, 0.3, 1.0, 3.0 and 9.0 mM of $Zn^{2+}$. As a control, a reaction without additional $Zn^{2+}$ was performed as well.

For this experiment, bottles were filled with 25 g of reaction mixture, each reaction mixture containing 2.5 g of DL-α-methylphenylglycine amide (end concentration 10 wt %), 46 µl from *O. anthropi* NCIMB 40321 batch no. LAM00101, and either no additional $ZnSO_4$ or 0.1, 0.3, 1.0, 3.0, or 9.0 mM of $ZnSO_4$. The pH of all reaction mixtures was 6.5. The reactions were started by the addition of the enzyme liquid.

All reaction mixtures were incubated on an orbital shaker at 55° C. and 200 rpm. Directly after addition of the enzyme (t=0 hours) and after 1, 4 and 11 hours samples of 1 g were taken and transferred to vials containing 4 g of 1 M $H_3PO_4$ to immediately stop the reaction. The exact amount of sample and stop solution were both determined by weighing. After filtration over a 0.22 µM filter, concentrations of α-methylphenylglycine and α-methylphenylglycine amide were determined by HPLC according to the following protocol:
Column: Inertsil ODS-3 (3 µm) 50 mm*4.6 mm ID
Eluent: 50 mM $H_3PO_4$—NaOH, pH=2.5

Flow: 0.8 ml/min
Temp.: 40° C.
$V_{inj.}$: 15 μL
Detection: UV 210 nm

The results of this experiment are given in table 3, wherein the conversions (amount of amino acid formed as compared to the total amount of starting amino acid amide) of the reactions are given in relative conversions; the highest conversion was set at 100.

TABLE 3

Influence of the $Zn^{2+}$ concentration on the hydrolysis reaction of DL-α-methylphenylglycine amide by the L-amidase from *O. anthropi* NCIMB 40321 (batch no. LAM 0011).

| Entry | [$Zn^{2+}$] (mM) | Conversion after | | |
|---|---|---|---|---|
| | | 1 h | 4 h | 11 h |
| A | 9.0 | 28 | 85 | 100 |
| B | 3.0 | 24 | 87 | 100 |
| C | 1.0 | 19 | 83 | 100 |
| D | 0.3 | 16 | 74 | 97 |
| E | 0.1 | 11 | 61 | 92 |
| F | 0 | 1.4 | 3.1 | 5.3 |

From table 3 it can be concluded that the presence of $Zn^{2+}$ is strangely preferable for activity of the *O. anthropi* L-amidase towards DL-α-methylphenylglycine amide. Without additional $Zn^{2+}$, hardly any hydrolysis reaction of this substrate occurs (see entry F).

Example 3

Enantioselective Hydrolysis of DL-α-methylphenylglycine Amide in the Presence of Different Divalent Metal Ions at pH 6.5 Using L-amidase from *Ochrobactrum anthropi* NCIMB 40321

In a similar reaction set-up as for example 2, it was investigated whether additional $Zn^{2+}$ had a beneficial effect on the conversion of DL-α-methylphenylglycine amide with L-amidase from *O. anthropi* NCIMB 40321, which had been fermented without an excess of $Zn^{2+}$. The hydrolysis reactions were performed in the presence of equimolar amounts of $Mn^{2+}$ or $Zn^{2+}$. Furthermore, a control reaction was performed using the L-amidase from *O. anthropi* NCIMB 40321 fermented in the presence of an excess of $Zn^{2+}$.

Bottles were filled with 25 g of reaction mixture, each reaction mixture containing 2.5 g of DL-α-methylphenylglycine amide (end concentration 10 wt %), 240 μl of L-amidase from *O. anthropi* NCIMB 40321 preparation LAM0001, and 1 mM of either $MnSO_4$ or $ZnSO_4$. A third reaction mixture was prepared containing (besides the substrate), 1 mM of $Zn^{2+}$ and 92 μl of L-amidase from *O. anthropi* NCIMB 40321 preparation LAM0011 (92 μl LAM0011 corresponds to the L-amidase activity of 240 μl LAM0001). Substrate incubation, sampling and analyses were all performed as described in example 2. Results of this experiment are given in table 4, wherein the conversions (amount of amino acid formed as compared to the starting amino acid amide) of the reactions are given in relative conversions; the highest conversion was set at 100.

TABLE 4

Effect of the $Zn^{2+}$ and $Mn^{2+}$ addition on the hydrolysis reaction of DL-α-methylphenylglycine amide by the L-amidase from *O. anthropi* NCIMB 40321 fermented in the absence of $Zn^{2+}$ in feed 1 (batch no. LAM 0001) and fermented with $Zn^{2+}$ in feed 1 (batch no. LAM 0011).

| Entry | Enzyme preparation | Metal ion | Conversion after | | |
|---|---|---|---|---|---|
| | | | 1 h | 3 h | 5 h |
| A | LAM0001 | $Mn^{2+}$ | 11 | 33 | 55 |
| B | LAM0001 | $Zn^{2+}$ | 33 | 94 | 100 |
| C | LAM0011 | $Zn^{2+}$ | 36 | 93 | 100 |

From table 4 it can be concluded that in the presence of 1 mM of $Zn^{2+}$, the rates of conversion of DL-α-methylphenylglycine amide with the enzymes fermented with and without extra $Zn^{2+}$ are similar and are both higher than the conversion in the presence of 1 mM $Mn^{2+}$.

Example 4

Enantioselective Hydrolysis of DL-tert-leucine Amide in the Presence of Different Divalent Metal Ions at pH 7.0 by L-amidase from *Ochrobactrum anthropi* NCIMB 40321

In a similar set-up as for example 2, the effect was determined of the presence of equimolar amounts of $Mn^{2+}$, $Zn^{2+}$, and $Mg^{2+}$ in the hydrolysis reaction of DL-tert-leucine amide with the L-amidase from *O. anthropi* NCIMB 40321. As a control, a reaction without any additional divalent metal ion was performed.

To perform this experiment, bottles were filled with 25 g of reaction mixture, each reaction mixture containing 3.13 g of DL-tert-leucine amide (end concentration 12.5 wt %), 1.45 ml of L-amidase from *O. anthropi* NCIMB 40321 (batch no. LAM0011), and 1.0 mM of $ZnSO_4$, $MgSO_4$ or $MnSO_4$. Furthermore, a separate reaction was performed without any additional divalent metal ion. The pH of all reaction mixtures was 7.0. The reactions were started by the addition of the enzyme liquid.

All reaction mixtures were incubated on an orbital shaker at 55° C. and 150 rpm. Directly after addition of the enzyme (t=0 hours) and after 1, 3 and 6.7 hours samples of 1 g were taken and transferred to vials containing 4 g of 1 M $H_3PO_4$ to immediately stop the reaction. Both the exact amount of sample and stop solution were determined by weighing. After filtration over a 0.22 μM filter, concentrations of tert-leucine and tert-leucine amide were determined by HPLC according to the following protocol:

Column: Inertsil ODS-3 (150 mm×4.6 mm I.D., 5μ), supplied by Varian-Chrompack
Eluent: 99 v/v % 50 mM $H_3PO_4$, pH=2.3 using 1N NaOH+1 v/v % acetonitrile
Flow: 1.0 ml/min
Temp.: 30° C.
$V_{inj.}$: 20 μl
Detection: fluorescence detection after post-column derivatization with OPA/MCE[a] ($\lambda_{ex}$ 365 nm and $\lambda_{em}$>420 nm).

(a) post-column derivatization was performed in a reaction coil (2 m×0.25 mm I.D.) at ambient temperature using 0.4 M borate buffer pH 10 containing o-phthalaldehyde (OPA) and 2-mercaptoethanol (MCE). The flow of the derivatization reagent was 1.0 ml/min. The reagent was prepared by first dissolving 49.46 g $H_3BO_3$ and 35 g KOH in 2 liter Milli-Q water, followed by adjustment of the pH to 10 using 1M KOH. Then 1.6 g OPA (in 20 ml ethanol) and 2 ml MCE were added to this borate buffer.

The results of this experiment are given in table 5, wherein the conversions (the amount of amino acid formed as compared to the amount of starting amino acid amide) of the reactions are given in relative conversions, the highest conversion was set at 100.

TABLE 5

Influence of the presence of different divalent metal ions on the hydrolysis reaction of DL-tert-leucine amide by the L-amidase from *O. anthropi* NCIMB 40321 (batch no. LAM 0011).

| Entry | Metal ion | Conversion after | | |
|---|---|---|---|---|
| | | 1 h | 3 h | 6.7 h |
| A | $Zn^{2+}$ | 15 | 56 | 100 |
| B | $Mg^{2+}$ | 8.9 | 32 | 77 |
| C | none | 8.1 | 30 | 69 |

The data in table 5 clearly show that in the presence of 1 mM of $Zn^{2+}$ a faster hydrolysis reaction of DL-tert-leucine amide by the L-amidase from *O. anthropi* NCIMB 40321 is obtained than in the presence of an equimolar amount of $Mg^{2+}$ or in the absence of an additional divalent metal ion.

Example 5

Enantioselective Hydrolysis of DL-tert-leucine Amide in the Presence of $Zn^{2+}$ at Different pH Values with L-amidase from *Ochrobactrum anthropi* NCIMB 40321

To investigate the influence of pH on the activity of L-amidase from *O. anthropi* NCIMB 40321 on the enantioselective hydrolysis of DL-tert-leucine amide, reactions in the presence and absence of 1 mM $Zn^{2+}$ were performed at pH 7.0, 8.0 and 9.0.

The whole experimental set-up was identical to the set-up of example 3. The results of these experiments are presented in table 6.

TABLE 6

Influence of the pH of the reaction mixture on the hydrolysis reaction of DL-tert-leucine amide in the presence and absence of 1 mM $ZnSO_4$ by the L-amidase from *O. anthropi* NCIMB 40321 (batch no. LAM 0011).

| Entry | pH | $Zn^{2+}$ (1 mM) | Conversion after | | |
|---|---|---|---|---|---|
| | | | 1 h | 3 h | 6.7 h |
| A | 7 | + | 15 | 56 | 100 |
| B | | − | 8.1 | 30 | 69 |
| C | 8 | + | 14 | 46 | 94 |
| D | | − | 11 | 38 | 82 |
| E | 9 | + | 14 | 43 | 93 |
| F | | − | 13 | 39 | 77 |

The invention claimed is:

1. An isolated nucleic acid molecule comprising a nucleotide sequence encoding an enantioselective amidase wherein said amidase has an amino acid sequence that has at least 95% identity with SEQ ID NO:2.

2. The nucleic acid molecule of claim 1, wherein said amino acid sequence is identical to SEQ ID NO:2.

3. The nucleic acid molecule of claim 1, wherein said encoding nucleotide sequence is operatively linked to one or more nucleotide sequences, which encode (a) marker polypeptide(s).

4. A vector comprising the nucleic acid molecule according to claim 1.

5. A microorganism modified to contain the nucleic acid molecule according to claim 1.

6. A process for the preparation of an enantioselective amidase, wherein said process comprises culturing the microorganism of claim 5 and isolating said enantioselective amidase.

7. A process for the fermentation of a microorganism in a fermentation medium, wherein said process comprises culturing said microorganism in a batch and a feed phase, wherein said microorganism expresses a nucleic acid sequence according to claim 1 and wherein between 0.5 and 50 mg/l $Zn^{2+}$ is fed per liter fermentation medium during the feed phase of the fermentation.

8. A process for the preparation of an enantiomerically enriched carboxylic acid and/or an enantiomerically enriched carboxylic acid amide, which comprises contacting a mixture of the corresponding D- and L-carboxylic acid amides with the amidase encoded by the nucleic acid molecule according to claim 1 in the presence of between 0.01 mM and 100 mM $Zn^{2+}$, whereby one of the enantiomers of the carboxylic acid amide is enantioselectively hydrolysed to form the corresponding enantiomerically enriched carboxylic acid, while the other enantiomer of the carboxylic acid amide remains unchanged.

9. An enantioselective amidase prepared by the process of claim 6.

10. An enantioselective amidase prepared by the process of claim 7.

11. A process for the preparation of an enantiomerically enriched carboxylic acid and/or an enantiomerically enriched carboxylic acid amide, which comprises contacting a mixture of the corresponding D- and L-carboxylic acid amides with the amidase of claim 9 in the presence of between 0.01 mM and 100 mM $Zn^{2+}$, whereby one of the enantiomers of the carboxylic acid amide is enantioselectively hydrolysed to form the corresponding enantiomerically enriched carboxylic acid, while the other enantiomer of the carboxylic acid amide remains unchanged.

12. A process for the preparation of an enantiomerically enriched carboxylic acid and/or an enantiomerically enriched carboxylic acid amide, which comprises contacting a mixture of the corresponding D- and L-carboxylic acid amides with the amidase of claim 10 in the presence of between 0.01 mM and 100 mM $Zn^{2+}$, whereby one of the enantiomers of the carboxylic acid amide is enantioselectively hydrolysed to form the corresponding enantiomerically enriched carboxylic acid, while the other enantiomer of the carboxylic acid amide remains unchanged.

* * * * *

SEQUENCE LISTING

<160> NUMBER OF SEQ ID NOS: 2

<210> SEQ ID NO 1
<211> LENGTH: 945
<212> TYPE: DNA
<213> ORGANISM: Ochrobactrum anthropi NCIMB 40321

<400> SEQUENCE: 1

```
atgtgcaata attgccatta caccattcac ggtcggcatc atcatttcgg ctgggacaac      60
tcgttccagc cggctgaaac ggtcgcgccc ggctcgaccc tgaaattcga atgtctggac     120
agcggcgcag gccactatca tcgcggcagc acagtcgccg atgtgtcgac gatggatttt     180
tccaaggtca atccggttac cggccccatc ttcgtcgatg gagccaaacc gggcgatgtc     240
ctgaaaatca ccatccacca gttcgagcca tcaggcttcg gctggacggc aaatattccg     300
ggcttcggtc ttctcgccga cgacttcaag gaaccggcgc tagcattgtg gaactacaat     360
cccacaacgc tggagccagc actcttcgga gagcgtgcgc gcgtgccgct gaagccgttc     420
gccggaacca tcggcgtcgc accggcggaa aagggcctgc attcggtcgt accaccgcgt     480
cgtgtcggcg gcaatctcga catccgcgat cttgcagccg gaaccacgct ttatctgccg     540
atcgaagtcg aaggcgcttt gttctccatt ggtgataccc atgcggcaca gggcgacggc     600
gaagtgtgcg gcaccgccat cgaaagcgcg atgaatgtcg ctctgacgct ggatctcatc     660
aaggatacgc cactgaagat gccccggttc accacgccgg ggccagtgac gcggcacctc     720
gataccaagg gttacgaagt caccaccggt atcgggtccg atctgtggga aggcgcgaaa     780
```

```
gccgccctct ccaacatgat cgacttctt tgccagacgc agaacctcaa cccggtggat    840
gcctatatgc tctgctcggc ctgcggtgat ctgcgtatca gcgaaatcgt cgatcagccg    900
aactgggtcg tatcgttcta cttcccgcgt tccgttttcg aataa                    945
```

<210> SEQ ID NO 2
<211> LENGTH: 314
<212> TYPE: PRT
<213> ORGANISM: Ochrobactrum anthropi NCIMB 40321

<400> SEQUENCE: 2

```
Met Cys Asn Asn Cys His Tyr Thr Ile His Gly Arg His His His Phe
 1               5                  10                  15

Gly Trp Asp Asn Ser Phe Gln Pro Ala Glu Thr Val Ala Pro Gly Ser
            20                  25                  30

Thr Leu Lys Phe Glu Cys Leu Asp Ser Gly Ala Gly His Tyr His Arg
        35                  40                  45

Gly Ser Thr Val Ala Asp Val Ser Thr Met Asp Phe Ser Lys Val Asn
    50                  55                  60

Pro Val Thr Gly Pro Ile Phe Val Asp Gly Ala Lys Pro Gly Asp Val
65                  70                  75                  80

Leu Lys Ile Thr Ile His Gln Phe Glu Pro Ser Gly Phe Gly Trp Thr
                85                  90                  95

Ala Asn Ile Pro Gly Phe Gly Leu Leu Ala Asp Asp Phe Lys Glu Pro
            100                 105                 110

Ala Leu Ala Leu Trp Asn Tyr Asn Pro Thr Thr Leu Glu Pro Ala Leu
        115                 120                 125

Phe Gly Glu Arg Ala Arg Val Pro Leu Lys Pro Phe Ala Gly Thr Ile
    130                 135                 140

Gly Val Ala Pro Ala Glu Lys Gly Leu His Ser Val Val Pro Pro Arg
145                 150                 155                 160

Arg Val Gly Gly Asn Leu Asp Ile Arg Asp Leu Ala Ala Gly Thr Thr
                165                 170                 175

Leu Tyr Leu Pro Ile Glu Val Glu Gly Ala Leu Phe Ser Ile Gly Asp
            180                 185                 190

Thr His Ala Ala Gln Gly Asp Gly Glu Val Cys Gly Thr Ala Ile Glu
        195                 200                 205

Ser Ala Met Asn Val Ala Leu Thr Leu Asp Leu Ile Lys Asp Thr Pro
    210                 215                 220

Leu Lys Met Pro Arg Phe Thr Thr Pro Gly Pro Val Thr Arg His Leu
225                 230                 235                 240

Asp Thr Lys Gly Tyr Glu Val Thr Thr Gly Ile Gly Ser Asp Leu Trp
                245                 250                 255

Glu Gly Ala Lys Ala Ala Leu Ser Asn Met Ile Asp Leu Leu Cys Gln
            260                 265                 270

Thr Gln Asn Leu Asn Pro Val Asp Ala Tyr Met Leu Cys Ser Ala Cys
        275                 280                 285

Gly Asp Leu Arg Ile Ser Glu Ile Val Asp Gln Pro Asn Trp Val Val
    290                 295                 300

Ser Phe Tyr Phe Pro Arg Ser Val Phe Glu
305                 310
```